United States Patent [19]

Ito

[11] Patent Number: 4,857,187

[45] Date of Patent: Aug. 15, 1989

[54] MULTISTAGE MIXER-SETTLER CENTRIFUGE

[75] Inventor: Yoichiro Ito, Bethesda, Md.

[73] Assignee: The Government of the U.S. as represented by the Secretary of the Department of Health and Human Services, Washington, D.C.

[21] Appl. No.: 101,970

[22] Filed: Sep. 28, 1987

[51] Int. Cl.⁴ .............................................. B01D 15/08
[52] U.S. Cl. ................................. 210/198.2; 210/635; 210/657
[58] Field of Search ............ 210/635, 656, 657, 198.2, 210/198.3; 55/67, 197, 386

[56] References Cited

U.S. PATENT DOCUMENTS

| | | | |
|---|---|---|---|
| 3,830,369 | 8/1974 | Pfadenhauer | 210/198.2 |
| 3,856,669 | 12/1974 | Ito | 210/198.2 |
| 3,994,805 | 11/1976 | Ito | 210/198.2 |
| 4,046,515 | 9/1977 | de Leeuw | 23/259 |
| 4,058,460 | 11/1977 | Ito | 210/198.2 |
| 4,151,089 | 4/1979 | Ito | 210/198.2 |
| 4,228,009 | 10/1980 | Ito | 210/198.2 |
| 4,422,941 | 12/1983 | Vaughan | 210/657 |
| 4,487,693 | 12/1984 | Ito | 210/198.2 |
| 4,510,058 | 4/1985 | Cais | 210/657 |
| 4,551,251 | 11/1985 | Kolobow et al. | 210/635 |

Primary Examiner—Ernest G. Therkorn
Attorney, Agent, or Firm—Browdy & Neimark

[57] ABSTRACT

A method and apparatus for chromatography employ a vibration driven mixing device mounted inside a column. One end of the mixing device is held in place by a stopper while the other end is free to vibrate back and forth. The mixture at the free end is efficiently mixed while the mixture at the held end remains undisturbed. The undisturbed portion can then be removed. This invention is particularly applicable to centrifugal chromatography where the vibration is produced by high frequency oscillation in the centrifugal force field.

7 Claims, 8 Drawing Sheets

MULTISTAGE MIXER-SETTLER CENTRIFUGE

FIELD OF THE INVENTION

This invention relates to countercurrent extraction, and more particularly to an elution system combining countercurrent distribution and countercurrent chromatography.

BACKGROUND OF THE INVENTION

Various separation methods have been applied to macromolecules and cell particles. Among the various processes, partition with aqueous/aqueous polymer phase systems has several desirable features; and consequently this method provides great advantage over other separation methods. Various types of new polymer phase systems have been introduced for separation of a variety of biological samples. However, high viscosity, low interfacial tension, and relatively low density difference between the two solvent phases have produced various technical problems in performing partition with the polymer phase systems. In general, these partition methods may be divided into two categories: one is the countercurrent distribution method (CCD) and the other is the countercurrent chromatography method (CCC).

CCD uses a discontinuous partition procedure consisting of the following three steps: mixing of the two solvent phases by shaking, settling them into two layers, and transfer of the mobile phase (usually the upper phase) of each partition unit to the next partition unit. Because of high viscosity and low interfacial tension between the two phases, the use of the conventional Craig apparatus becomes impractical due to the long settling times required. A substantial improvement in separation times has been achieved by introduction of a thin-layer countercurrent distribution apparatus which provides an extremely short settling distance of a few millimeters for each phase, thus reducing the settling time down to a few minutes. More recently, a fully automated centrifugal thin-layer CCD apparatus which permits both phase separation and transfer processes in a strong centrifugal force field has been designed. However, that method still requires a considerably long separation time of one theoretical plate or one operational cycle every two minutes.

CCC has also been used for partition of various biological samples under continuous elution of the mobile phase. The method generally uses a coiled column under a centrifugal force field. High speed CCC recently developed can yield an extremely high partition efficiency of one theoretical plate per second with conventional organic/aqueous two-phase solvent systems. However, when the method is applied to partition with aqueous/aqueous polymer phase systems, high viscosity of the polymer phases causes insufficient mixing of the two solvent phases in the coiled column resulting in poor peak resolution. Consequently, the method fails to produce significant improvement over the CCD method previously described. The best results have been obtained with a special type of the coil planet centrifuge called the nonsynchronous flow-through coil planet centrifuge which generates slow rotation of a coiled column under a strong centrifugal force field. However, this apparatus is extremely complex and expensive and in addition the applicable flow rate of the mobile phase is limited due to carry over of the stationary phase.

SUMMARY OF THE INVENTION

Accordingly, it is an object of the present invention to obviate problems of the prior art, such as discussed above.

It is another object of the present invention to provide for improved countercurrent extraction; and yet another object to provide a novel method and apparatus for countercurrent extraction.

It is a further object of the present invention to combine the advantages of the countercurrent distribution method (CCD) with the advantages of countercurrent chromatography (CCC).

The present invention introduces a separation column construction which enables efficient partitioning with aqueous/aqueous polymer phase systems and therefore permits universal application for separation and purification of various biological samples such as proteins, nucleic acids, polysaccharides, cell organelles, etc.

When a straight elastic rod (tubular or solid), one end of which is supported by a stopper, is inserted into the separation column, high frequency vibration will cause the free end of the rod to vibrate back and forth inside the column unit. This procedure efficient mixing of the two solvent phases, while in the phase at the opposite end of the rod (close to the stopper) the effect of the vibration is negligible leaving that phase relatively undisturbed. The rod should extend at least far enough into the receptacle to produce efficient mixing of the phase furthest from the stopper. Generally, the rod should extend for at least a majority of the length of the receptacle. Preferably, the rod should extend almost to the distal end of its receptacle.

In one embodiment of the invention, the above hydrodynamic effect can be effectively utilized for performing continuous partitioning by replacing the rod with a flow tube for elution of the mobile phase. Multiple units can be connected in series with flow tubes in such a way that the outlet of each receptacle tube extends toward the other end of each next tube. The mobile phase at the vicinity of the stopper, where the mixing effects is minimized, becomes almost free of the stationary lower phase and is then transferred to the next column unit to repeat the process. Finally, all the column units reach hydrostatic equilibrium and thereafter the mobile phase is collected from the outlet of the column. Similar hydrodynamic process can be observed with the lower phase eluting through an inverted column.

DESCRIPTION OF THE PREFERRED EMBODIMENTS

Figures 1A, 1B:
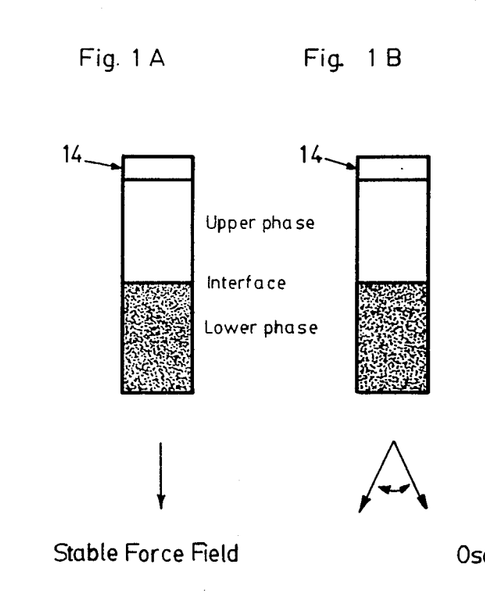
FIGS. 1A–1D show cross-sectional views of chromatography columns before and after the introduction of a mixing rod.
Figures 1C, 1D:
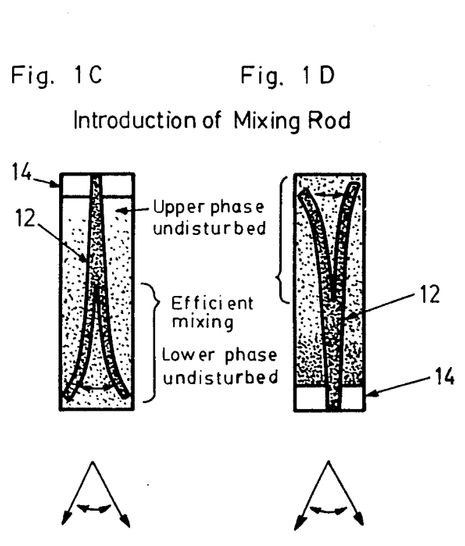

FIGS. 1A–1C illustrate the general principle of the present invention. In FIG. 1A a column unit contains nearly equal volumes of two solvent phases which are separated by a stable force field as indicated by an arrow at the bottom. Application of an oscillating force field at a high frequency fails to mix the two solvent layers because of their high viscosity as indicated in FIG. 1B. However, when a straight elastic rod 12, one end of which is supported by a stopper 14, is inserted, the high frequency vibration causes the free end of the rod 12 to vibrate back and forth inside the column unit producing efficient mixing of the two solvent phases (FIGS. 1C and 1D), while at the opposite end of the rod the effect of vibration becomes negligible leaving the upper (FIG. 1C) or the lower (FIG. 1D) phae undisturbed as illustrated.

Figure 2A:
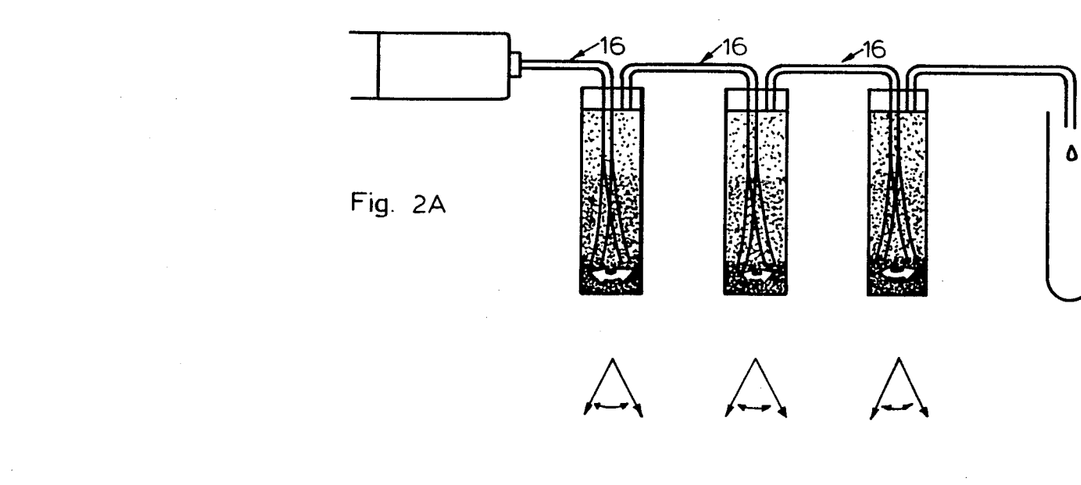
FIGS. 2A and 2B show cross-sectional views of three column units connected in series with flexible flow tubes acting as the mixing rods according to the present invention.
Figure 2B:
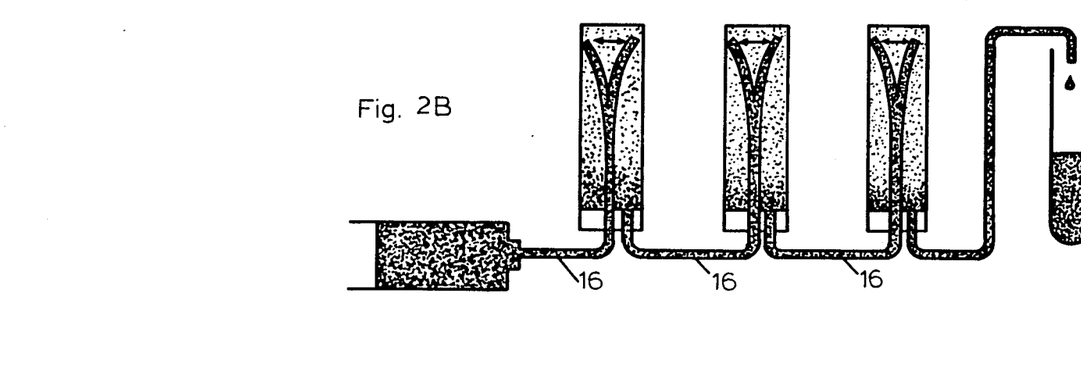

The above hydrodynamic effect can be effectively utilized for performing continuous partitioning by replacing the rod 12 with a flow tube 16 for elution of the mobile phase as shown in FIGS. 2A and 2B where three column units are connected in series with flow tubes 16 in such a way that the outlet of each tube extends toward the other end of column unit as illustrated in FIGS. 2A and 2B. In FIG. 2A the column is first completely filled with the lower stationary phase (dark) and the upper mobile phase is eluted with a pump while applying an oscillating force field to induce vibration of the free end of the flow tube. As the mobile phase enters the first column unit through the vibrating flow tube 16, it is immediately dispersed and mixed with the stationary phase to establish a hydrostatic equilibrium of the two solvent phases where the mixing effects of the vibrating flow tube and the settling effects of the force field are balanced to form a density gradient of the two solvent phases along the length of the column unit. The mobile phase at the vicinity of the stopper, where the mixing effects is minimized, becomes almost free of the stationary lower phase and is then transferred to the next column unit to repeat the process. Finally, all three column units reach the hydrostatic equilibrium and thereafter the mobile phase is collected from the outlet of the column. Similar hydrodynamic process can be observed with the lower phase eluting through the inverted column as shown in FIG. 2B. In either elution mode (FIGS. 2A and 2B), samples introduced locally at the inlet of the column are continuously subjected to an efficient partition process between the two phases and separated according to their partition coefficients.

Figure 3:
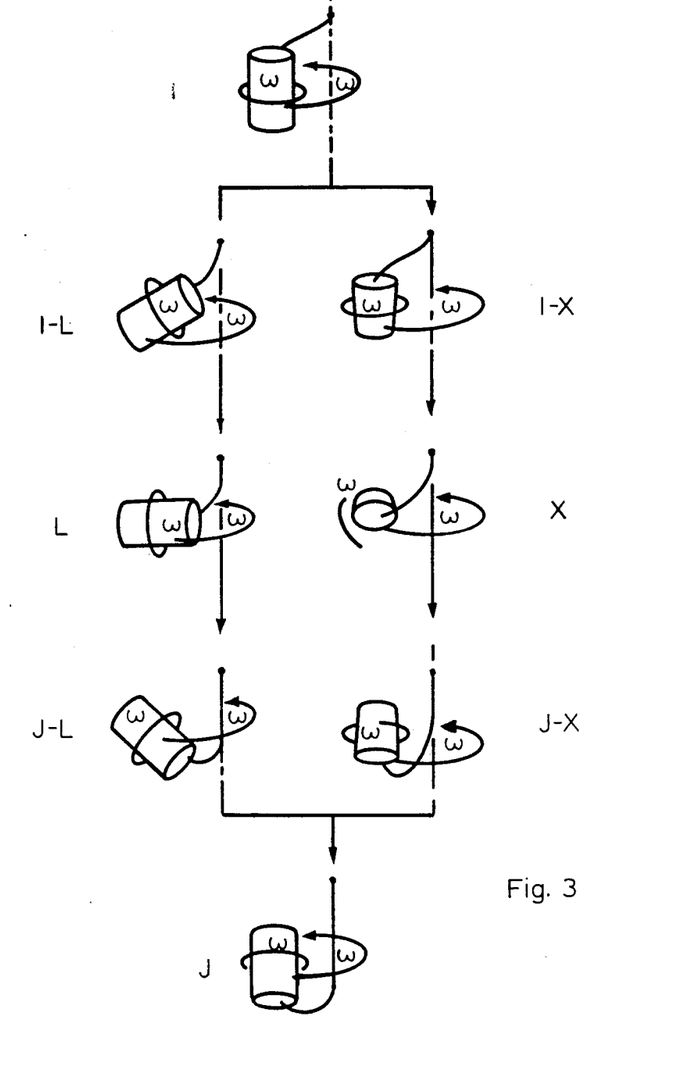
FIG. 3 is a diagram of the motion developed in various synchronous coil planet centrifuges.

The present method can satisfactorily utilize the flowthrough coil planet centrifuges which have been developed for performing CCC with conventional two-phase solvents systems. Among various synchronous coil planet centrifuges illustrated in FIG. 3, four schemes including types J, J-L, L, and X may provide a suitable oscillating force field with sufficient strength required for phase settling.

Figure 4:
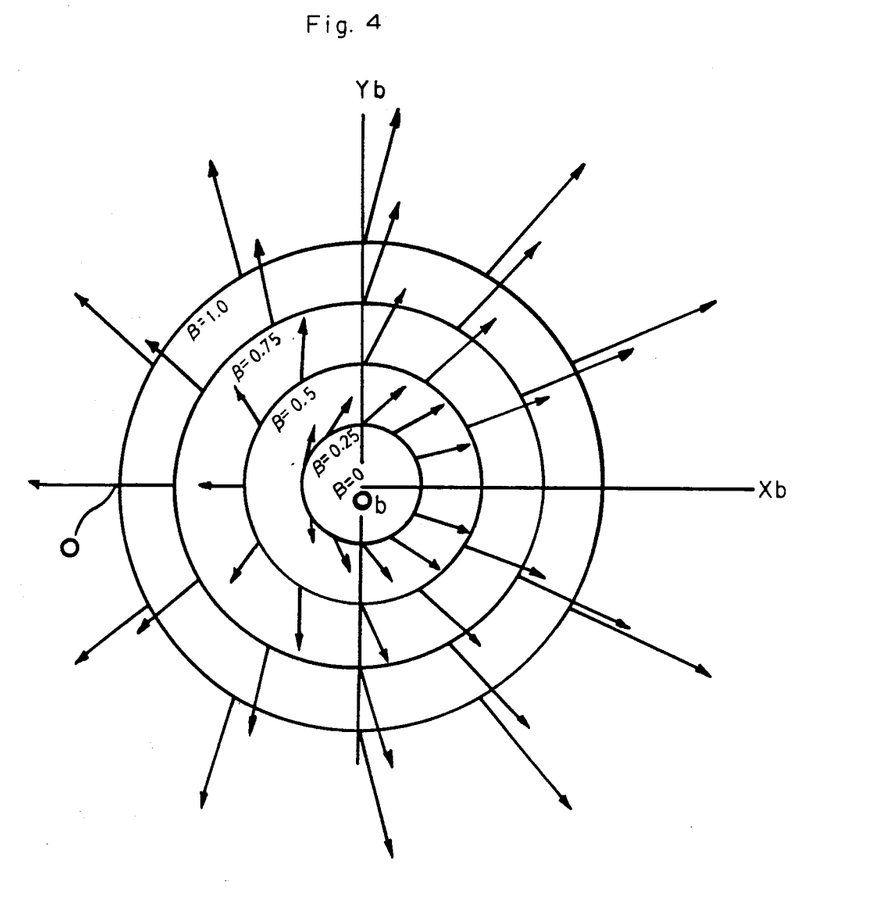
FIG. 4 is a diagram of the typical centrifugal force field generated by Type J synchronous planetary motion.

A typical centrifugal force field generated by Type J synchronous planetary motion is shown in FIG. 4 where point O indicates the center of revolution (center of the centrifuge) and point $O_b$, the center rotation (center of the holder). Several concentric circles indicate the location of the point on the holder, i.e., $B=r/R$ where r is the radius of the holder and R, the radius of centrifuge arm. As shown by distribution of th centrifugal force vectors (arrows), strength of the field increases B values while accompanied by reduced amplitude of oscillation.

Figure 5:
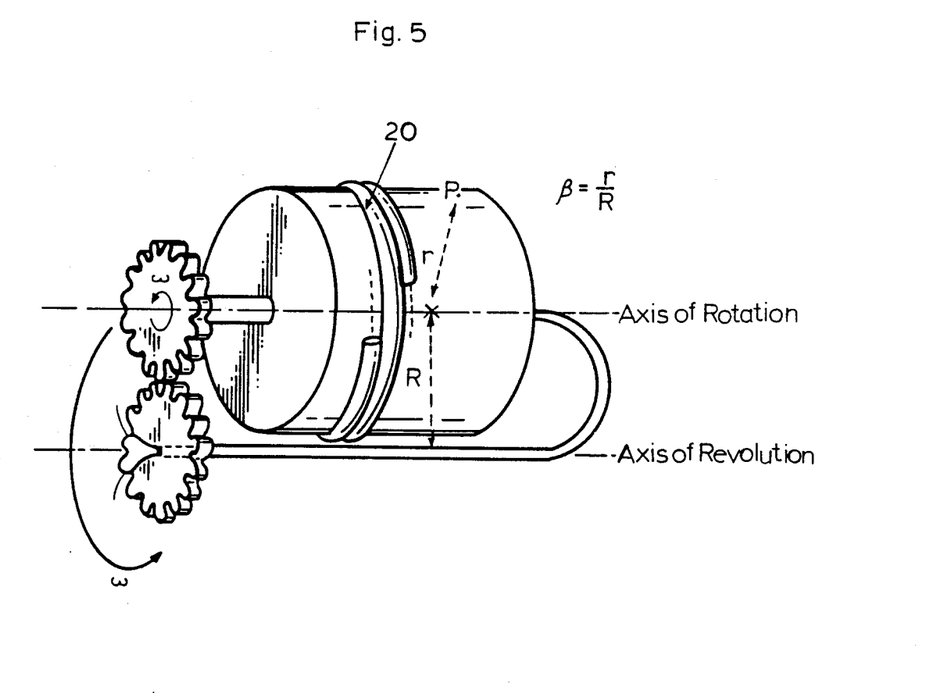
FIG. 5 is a diagram of the design principle of a Type J centrifuge.

The design principle of the Type J centrifuge is shown in FIG. 5. A cylindical holder is equipped with a planetary gear which is coupled to an identical stationary sun gear mounted on the central axis of the centrifuge. This gear coupling produces the desired planetary motion of the holder as indicated by a pair of arrows. The coiled column 20 on the holder is replaced by the multistage mixer-settler column in the present invention.

Figure 6:
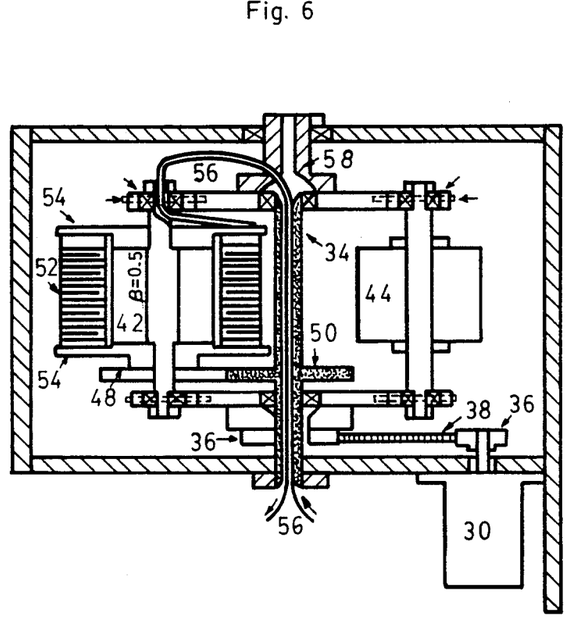
FIG. 6 shows a cross-sectional view of the Type J coil planet centrifuge which can be employed to provide a strong oscillating centrifugal force field according to the present invention.

FIG. 6 shows a cross-sectional view of a planet centrifuge (Type J) which can provide a strong oscillating centrifugal force field and therefore is useful for the present purpose. The motor 30 drives the rotary frame around the central stationary pipe 34 (shaded) via a pair of toothed pulleys 36 and toothed 38 belt. The rotary frame consists of a pair of aluminum plates rigidly bridged with links (not shown in the diagram) and holds a column holder 42 and a counterweight holder 44 in the symmetrical positions at 10 cm from the central axis of the centrifuge. The column hoder shaft is equipped with a planetary gear 48 which is coupled with an identical stationary sun gear 50 mounted around the central stationary pipe 34. This gear coupling produces the desired planetary motion of the holder 42 as was shown in FIG. 5. The multistage mixer-settler column 52 is mounted on the holder rigidly between a pair of flanges 54. The feed and return flow tubes 56 connected to the column are first led through the center hold of the holder shaft and then making a loop reach the side-hold of the short coupling pipe 58 to enter the opening of the central stationary pipe as illustrated in FIG. 6. These flow tubes can rotate freely around the central axis of the centrifuge without twisting.

Figure 7A:
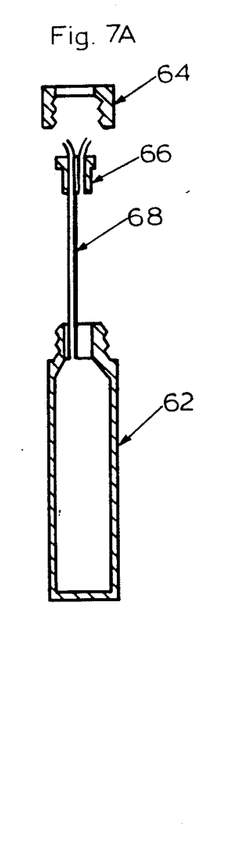
FIGS. 7A–7C show cross-sectional views of possible column designs according to the present invention.
Figure 7B:
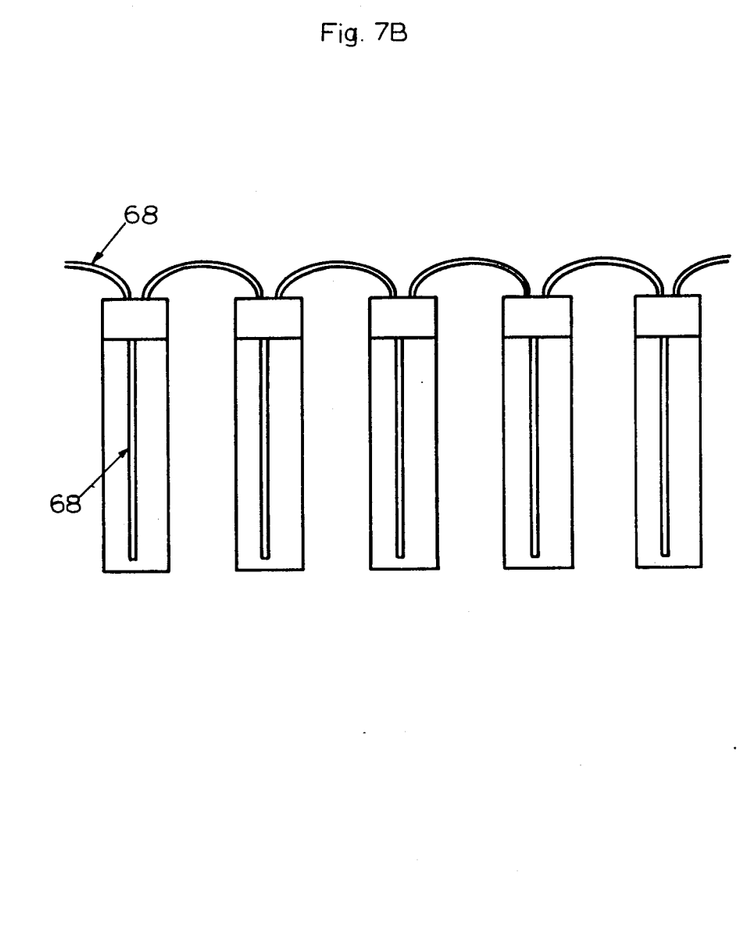
Figure 7C:
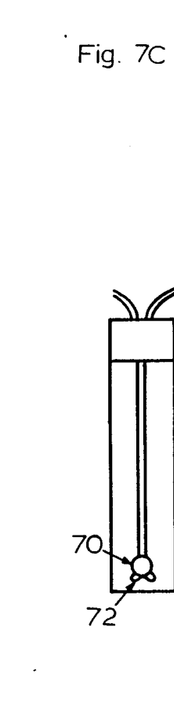
Figure 8:
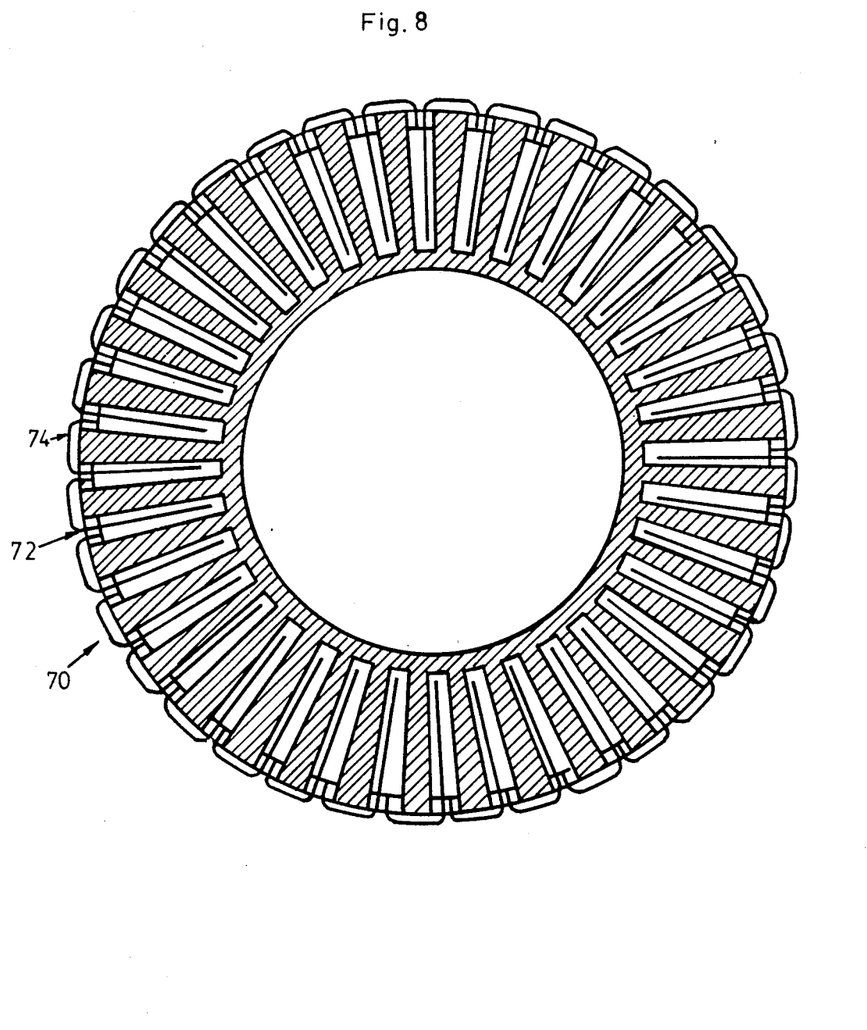
FIG. 8 shows a cross-sectional view of a block with cavities in it according to the present invention.

The separation column based on the principle described in FIG. 2 can be made in various ways. FIGS. 7A–7C show one embodiment of the column design. The column unit in FIG. 7A is made from a glass sample bottle 62 equipped with a perforated screw cap 64 and a teflon stopper 66. The flow tubes 68 are inserted into the bottle cavity through the holes of the teflon stopper which tightly fit to the tubing. A series of column units (FIG. 7B) is arranged radially into a plastic mold which is supported between the flanges on the holder. The response of the flow tubes to high frequency vibration can be enhanced by attaching a weight 70, typically a glass of teflon bead, at the tip of the flow tube held in place with a flanged top 72 as shown in FIG. 7C. The column can also be made by making multiple cylindrical cavities directly into a inert plastic block 70 such as Kel-F (trifluoromonochloroethylene) and closing the opening with stoppers 72 equipped with flow tubes 74 as illustrated in FIG. 8.

In each separation the column is filled with the stationary phase and the sample solution is locally introduced at the inlet of the column. Then, the apparatus is rotated at a given speed typically 800–1000 rpm while the mobile phase is eluted through the column. The effluent from the outlet of the column is continuously monitored with a UV monitor and fractionated into test tubes with a fraction collector.

Various changes can be made without departing from the scope of the invention and the invention is not to be considered limited to what is described in the specification and drawings.

What is claimed is:

1. A planetary centrifuge comprising a separation column comprising a plurality of essentially cylindrical receptacles connected in series between a supply means and a collection means by a plurality of flow tubes;

at least one of said flow tube being for transferring a mobile phase from said supply means to the first receptacle in said series;

at least another one of said flow tubes being for transferring a mobile phase from the last receptacle of said series to said collection means;

the remainder of said flow tubes being for transferring a mobile phase from one receptacle in said series to the succeeding receptacle in said series;

mixing means with each said receptacle comprising an elastic elongated rod having a free end within said receptacle and a fixed end, outside said receptacle, said rod extending axially within said receptacle for at least a majority of the depth of said receptacle, said free end of said rod being adapted to oscillate when its respective receptacle is subjected to an oscillating force field;

the flow tubes and rods extending through one end of said receptacles; and the separation column being mounted about a column holder so that the cylindrical axes of said receptacles are radially oriented with respect to a central axis said column holder about which said column holder is rotatable, said column holder being fixed within a frame so as to be revolvable about a planetary axis spaced way form said central axis.

2. The planetary centrifuge of claim 1, wherein said mixing means comprises a solid rod.

3. The planetary centrifuge of claim 1, wherein said mixing means comprises one of said flow tubes.

4. The planetary centrifuge of claim 1, wherein said free end of said rod extends axially almost to one end of said receptacle most distal said fixed end of receptacle.

5. The planetary centrifuge of claim 1, wherein plurality of receptacles are arranged in a plurality of longitudinally extending rows upon said column holder.

6. The planetary centrifuge of claim 5, wherein a weight is attached to the free end of said rod.

7. The planetary centrifuge of claim 1, wherein at least one end of said receptacle is sealed by a stopper, said flow tubes and rod connected to said receptacles extending through and being fixed within said stopper.

* * * * *